US009924970B2

(12) United States Patent
Gordon

(10) Patent No.: US 9,924,970 B2
(45) Date of Patent: Mar. 27, 2018

(54) DEVICE AND METHOD FOR TREATMENT OF SPINAL DEFORMITY

(71) Applicant: GLOBUS MEDICAL, INC., Audubon, PA (US)

(72) Inventor: Jeffrey David Gordon, Newtown Square, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 14/930,800

(22) Filed: Nov. 3, 2015

(65) Prior Publication Data

US 2016/0051286 A1    Feb. 25, 2016

Related U.S. Application Data

(63) Continuation-in-part of application No. 14/039,660, filed on Sep. 27, 2013.

(60) Provisional application No. 61/744,525, filed on Sep. 28, 2012.

(51) Int. Cl.
*A61B 17/70* (2006.01)
*A61B 17/80* (2006.01)

(52) U.S. Cl.
CPC ...... *A61B 17/7022* (2013.01); *A61B 17/7001* (2013.01); *A61B 17/701* (2013.01); *A61B 17/7002* (2013.01); *A61B 17/705* (2013.01); *A61B 17/7007* (2013.01); *A61B 17/7053* (2013.01); *A61B 17/7055* (2013.01); *A61B 17/809* (2013.01); *A61B 17/7067* (2013.01); *A61B 17/7068* (2013.01)

(58) Field of Classification Search
CPC ............ A61B 17/7055; A61B 17/7019; A61B 17/7022; A61B 17/7031; A61B 17/7029; A61B 17/7026; A61B 17/842; A61B 17/8645; A61B 17/7049; A61B 17/705; A61B 17/7053; A61B 2050/007; A61B 2050/0074
USPC ........................... 403/71, 196, 234, 256, 261
See application file for complete search history.

(56) References Cited

U.S. PATENT DOCUMENTS

| | | | |
|---|---|---|---|
| 8,579,901 B1 * | 11/2013 | Foerster ................. | A61B 17/82 606/74 |
| 2004/0133203 A1 * | 7/2004 | Young ................ | A61B 17/7052 606/253 |
| 2009/0105715 A1 * | 4/2009 | Belliard ............. | A61B 17/8869 606/103 |
| 2014/0094851 A1 * | 4/2014 | Gordon .............. | A61B 17/7001 606/264 |

FOREIGN PATENT DOCUMENTS

| | | |
|---|---|---|
| KR | 1020090058371 A | 6/2009 |
| WO | 1993007823 A1 | 4/1993 |
| WO | 2005018470 A1 | 3/2005 |
| WO | 2008013623 A2 | 1/2008 |

\* cited by examiner

*Primary Examiner* — Julianna N Harvey

(57) ABSTRACT

The present invention generally relates to methods and device for treatment of spinal deformity, wherein at least one tether is utilized to maintain the distance between the spine and the an ilium to (1) prevent increase in abnormal spinal curvature, (2) slow progression of abnormal curvature, and/ or (3) impose at least one corrective displacement and/or rotation.

15 Claims, 19 Drawing Sheets

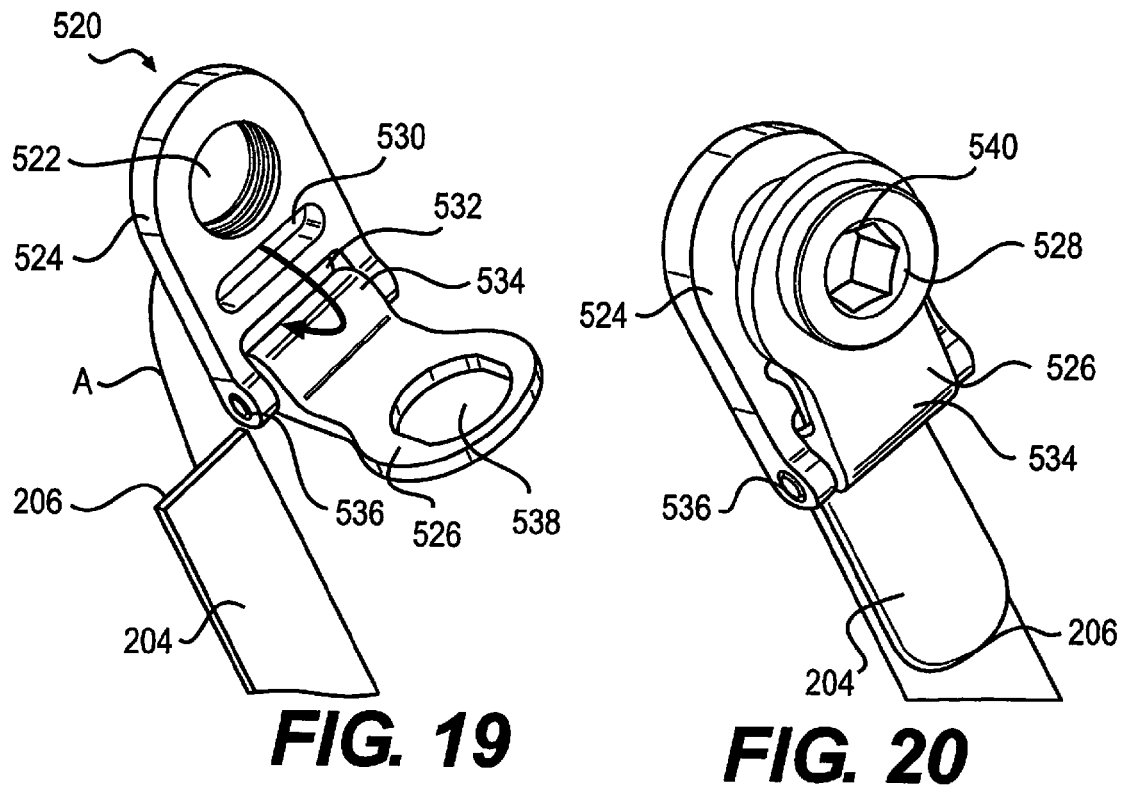
FIG. 19   FIG. 20
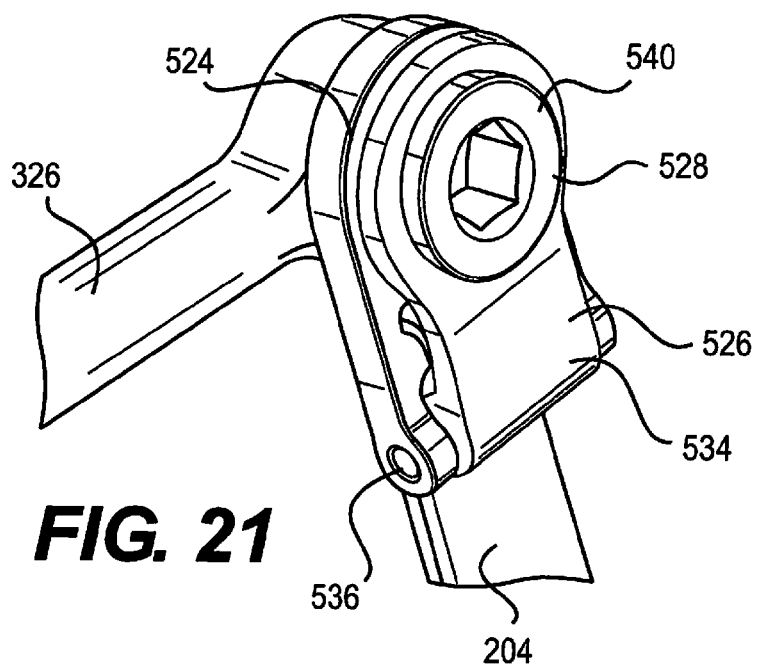
FIG. 21

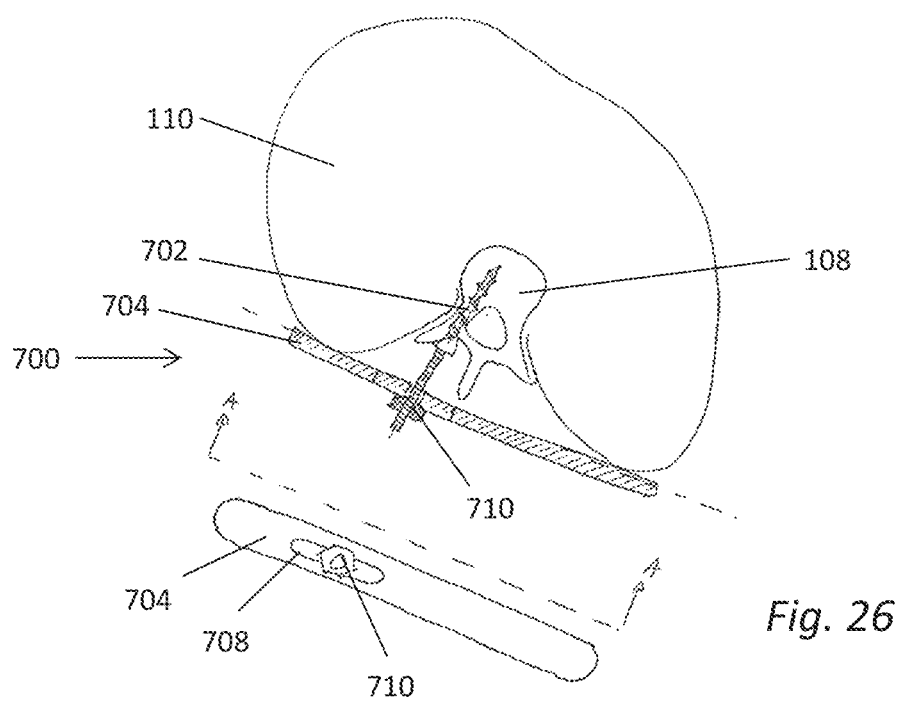
Fig. 26
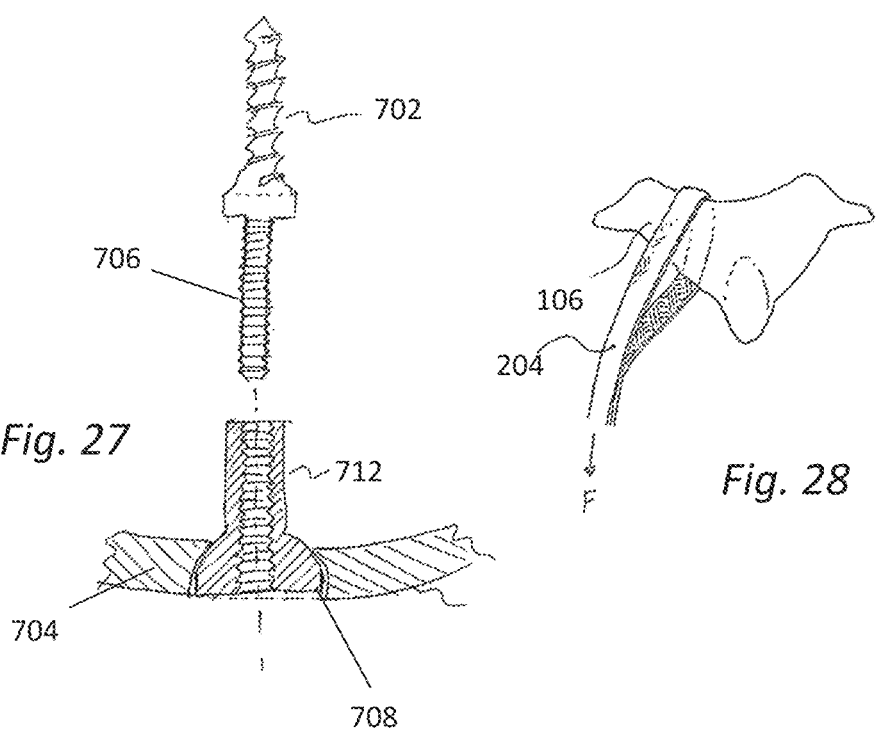
Fig. 27
Fig. 28

DEVICE AND METHOD FOR TREATMENT OF SPINAL DEFORMITY

CROSS-REFERENCE TO RELATED APPLICATIONS

This patent application is a continuation-in-part of U.S. application Ser. No. 14/039,660, filed Sep. 27, 2013, which claims priority to U.S. Provisional Application Ser. No. 61/744,525 filed on Sep. 28, 2012, the contents of which are hereby incorporated by reference in their entireties for all purposes.

FIELD OF THE INVENTION

The present invention generally relates to methods and devices for treatment of spinal deformity.

BACKGROUND OF THE INVENTION

Scoliosis is a spinal deformity characterized by an abnormal curvature of the spine in the coronal plane. Adolescent idiopathic scoliosis (AIS) is the most prevalent type of scoliosis which develops during adolescence in an otherwise healthy patient and typically ceases at the onset of skeletal maturity. The cause of the disease is presently unknown.

Current surgical treatment of scoliosis involves manipulation of the spinal column and attachment of corrective devices for fusion of a portion of the spine. One such system, the Cotel-Dubousset system utilizes rigid metal rods attached to the spine. The rods are manipulated during surgery in an attempt to reduce abnormal curvatures and rotations of the spinal column. Large loads are exerted on the spine for correction which risks the patient's neurological condition. Recovery from these procedures can be lengthy and painful. Also, if normal lordosis and kyphosis are not restored, a condition called "flat back syndrome" may occur causing chronic pain. Even a successful procedure rarely results in a normal spinal curvature and the patient is left with an immobile spinal section. The discs above and below the fusion zone are at risk of future degeneration due to the increased mechanical demands placed on them.

It is therefore evident that there are flaws in prior art methods and devices. Most prior art devices are part of the load path of the spinal column. For example, it is understood that the Cotel-Dubgousset system rigidly attaches stiff metal rods to the spine. A structure having two roughly parallel support members relies primarily on the stiffer of the two members for transmission of loads. Therefore, loads exerted on an instrumented spine are transferred through the implant instead of through the spine. Spinal loads can be significantly large, and the implants will not support such loads indefinitely. Fatigue failure of the implant will occur if fusion is delayed.

Therefore, there is an unaddressed need that exists to provide a new and better system for correcting spinal deformities.

SUMMARY OF THE INVENTION

The current invention describes methods and devices for treating spinal deformity which offer significant improvements over prior art methods and devices. In general terms the present invention is used to secure the distance between an ilium and the spine to either correct or maintain spinal curvature. There are many embodiments of the invention which will achieve the stated objectives, some of which will be presented in the following summary.

In one embodiment of the invention, at least one device is attached between the spine and the pelvis which incorporates at least one flexible tether. Attachment of the flexible tether to the spine and ilium involves implantation of anchoring means and then attachment of the tether to the anchoring means. For example, at least one bone screw, pedicle screw, cannulated bone screw, clamp, plate, bone anchor, or shackle might be anchored to at least one vertebra and another to a portion of the ilium and the flexible tether may be attached to both. Other means of attachment will be clear to one practiced in the art. Alternatively, a loop of material may be placed around a bony structure (e.g. spinous process, transverse process, lamina or pars) or a hole through a bony structure through which the flexible tether is passed.

It should be noted that the present invention enables manipulating the vertebral column to correct the deformity by securing the tether to a portion of the ilium and a portion of the vertebral column; the ability to correct deformity by correcting the effective length of the tether between the ilium and vertebra over time; and correcting deformity by the natural growth of the spine by allowing the tether to maintain effective length between the vertebral column and the ilium.

Adjustment of the distance between the spine and ilium is achieved by varying the location at which the tether is attached to the anchoring means. The tether does not change lengths during the adjustment process, but the distance between the attachment points does, much like adjusting a belt around your waist. Taking advantage of the inherent viscoelasticity of spinal structures, the curvature may be gradually corrected by small incremental corrections over a protracted period of time, whereby the original incision is re-opened, or a new incision next to the original incision is created and the attachment means is disengage and then reengaged at a different location along the tether. Alternatively the patient's growth may be used to achieve correction.

Alternatively, the tether may branch into multiple tethers to provide multiple attachments to the spine and/or ilium. If more than one tether is used, each can be attached to a different vertebra, or multiple tethers can be attached to the same vertebra. Tethers can be attached to either or both sides of the vertebral column and either opposing sides of ilium as needed to generate correction of the spinal deformity. A crossing pattern whereby a tether is attached to the right side of the vertebra (e.g. the right pedicle) and left ilia, or vice versa, is possible. Also, a tether may be attached to a vertebra and then passed through an eye screw or other guiding device which is attached to the ilium (or both ilia) and then attached to a second vertebra with a pedicle screw or other means. In can be envisioned by one skilled in the art that guiding devices may be utilized on a number of vertebrae or one the ilium or ilia. The tether may also originate with an attachment to the pelvis, pass through any number of guide members attached to the spine, and then terminate at the pelvis again.

According to another embodiment, a spinal system for correcting a deformity in the spine includes a tether, an anchor, an elongate rod and two bone fasteners, a clamp, and a fastener. The clamp is securable to the elongate rod. The clamp includes a clamp body and a hasp body hingedly connected to the clamp body. The clamp body has a first opening extending through the clamp body, and the hasp body has a second opening extending through the hasp body.

When the clamp is closed, the first and second openings are aligned with one another, and the fastener is configured to be received through the first and second openings to securely lock the tether within the clamp. The hasp body may include a hinge sleeve portion having an opening extending therethrough, and a pivot pin received in the opening and connected to the clamp body to allow for pivotal movement of the hasp body relative to the clamp body. The tether may be temporarily secured to the clamp body, before the clamp is closed, by first and second elongate slots extending through the clamp body, which are configured to receive the tether. Alternatively, the clamp body may include an elongate pin member with opposing ends configured to be received in the clamp body so that the tether wraps around the elongate pin to temporarily secure the tether in the clamp.

These and other aspects of the present invention will become apparent from the following description of the embodiments taken in conjunction with the following drawings, although variations and modifications therein may be affected without departing from the spirit and scope of the novel concepts of the disclosure.

The present invention provides an improved method of arresting a spinal deformity whereby at least one device is surgically attached between the spine and the ilium. Also, the present invention provides a system and a method for correcting a spinal deformity whereby at least one device is surgically attached between the spine and the ilium. One method of adjusting the curvature of the spine without fusion may include, for example, installing an anchor into a portion of the ilium; installing two bone fasteners into the pedicles of a vertebra and connecting an elongate rod between the two bone fasteners; attaching a first end of a tether to the anchor; attaching a second end of the tether to a clamp, the clamp having a clamp body and a hasp body hingedly connected to the clamp body, the clamp body having a first opening extending through the clamp body, and the hasp body having a second opening extending through the hasp body; closing the clamp such that the first and second openings are aligned with one another; inserting a fastener through the first and second openings to securely lock the tether within the clamp; and connecting the clamp to the elongate rod. Another method of adjusting the curvature of the spine without fusion may include axially rotating one or more vertebra to produce a lateral shift in the spine.

BRIEF DESCRIPTION OF THE DRAWINGS

The present invention will become more fully understood from the detailed description and the accompanying drawings, wherein:

FIGS. 19-21 illustrate an alternative embodiment of a tether clamp;

FIGS. 26 and 27 show a method and device for correcting scoliosis by de-rotating the vertebra in the axial plane; and FIG. 28 depicts an alternative version of coupling the tether to the spine by looping the tether around the lamina.

DETAILED DESCRIPTION OF THE PREFERRED EMBODIMENTS

The following description of the preferred embodiment(s) is merely exemplary in nature and is in no way intended to limit the invention, its application, or uses. The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

Figure 1:
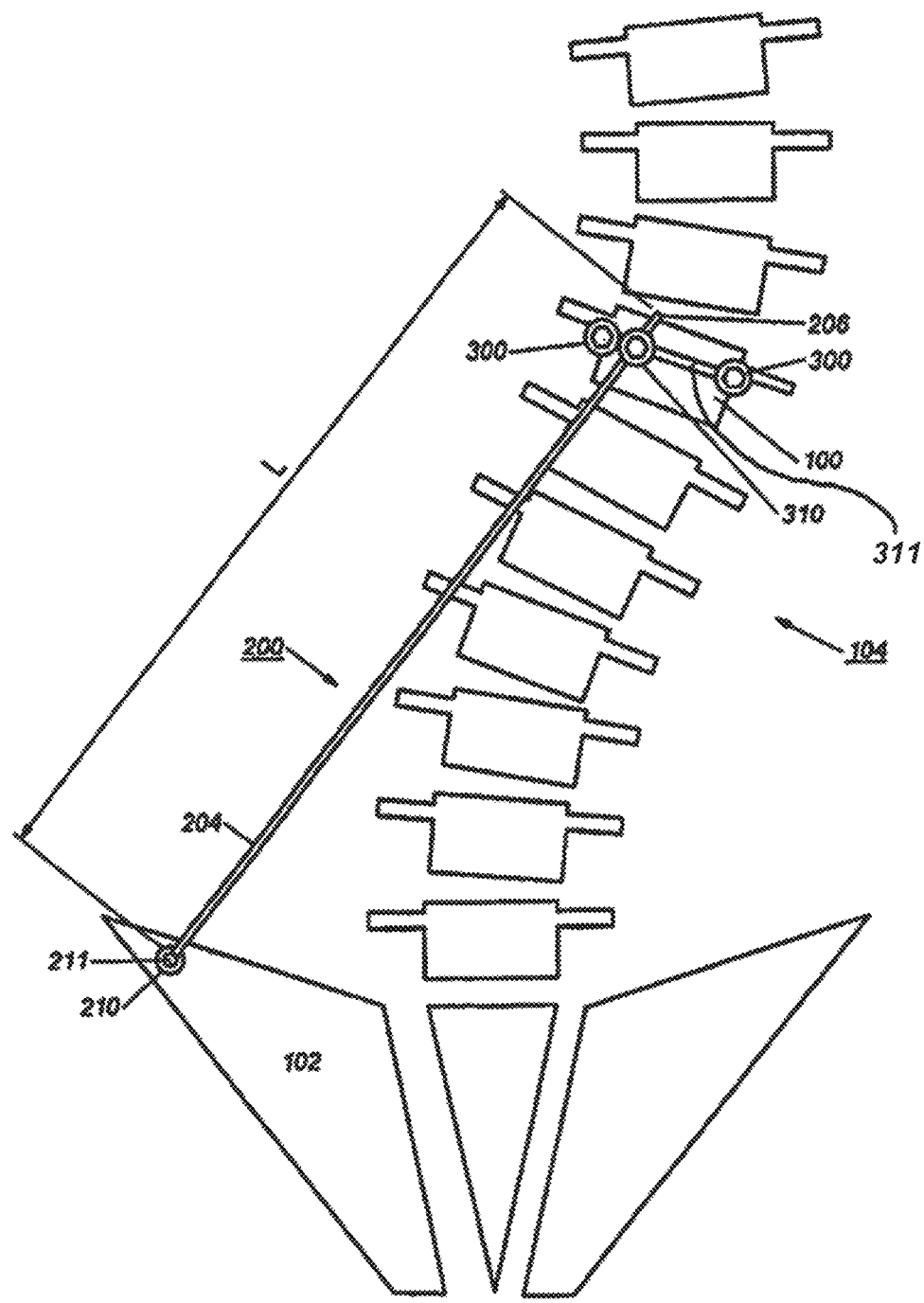
FIG. 1 is an illustration of a posterior view of a deformed human spine with an implanted device according to one embodiment of the present invention.

FIG. 1 is an illustration of a posterior view of a deformed spine 104 whereby the preferred embodiment of the device 200 is attached to an ilium 102 and a vertebra 100. Device 200 includes a tether 204 having a free end 206 and that is configured to be attached to the ilium and a portion of the vertebra. Specifically, in one embodiment, two attachment mechanisms such as pedicle screws 300 are anchored to the vertebra of the spine by insertion into opposing pedicles, and a transverse rod 311 is attached to the pedicle screws 300. It should be noted that although pedicle screws are provided in this particular embodiment, any other type of anchoring mechanism such as hooks may also be used. A tether clamp 310 is attached to rod 311 and the tether 204 is passed though tether clamp 310 and then passed down to the ilium 102 thereby securing a connection between the attached vertebra and the ilium. To attach the tether 204 to the ilium 102, an ilium anchor 210 is provided. The ilium anchor 210 includes a bore 211 and is configured to be attached to the ilium by inserting the anchor 210 (threading) into a hole which has been drilled or punched through the ilium 102. It should be noted that any other similar mechanism to attach anchor 210 to the ilium 102 may also be utilized. Tether 204 is passed through hole or bore 211 in the ilium anchor 210 and then brought back to the vertebra 100 and passed again through the tether clamp 310. In other embodiments, the tether 204 may only be passed once through the tether clamp and ilium anchor 210.

Figure 2:
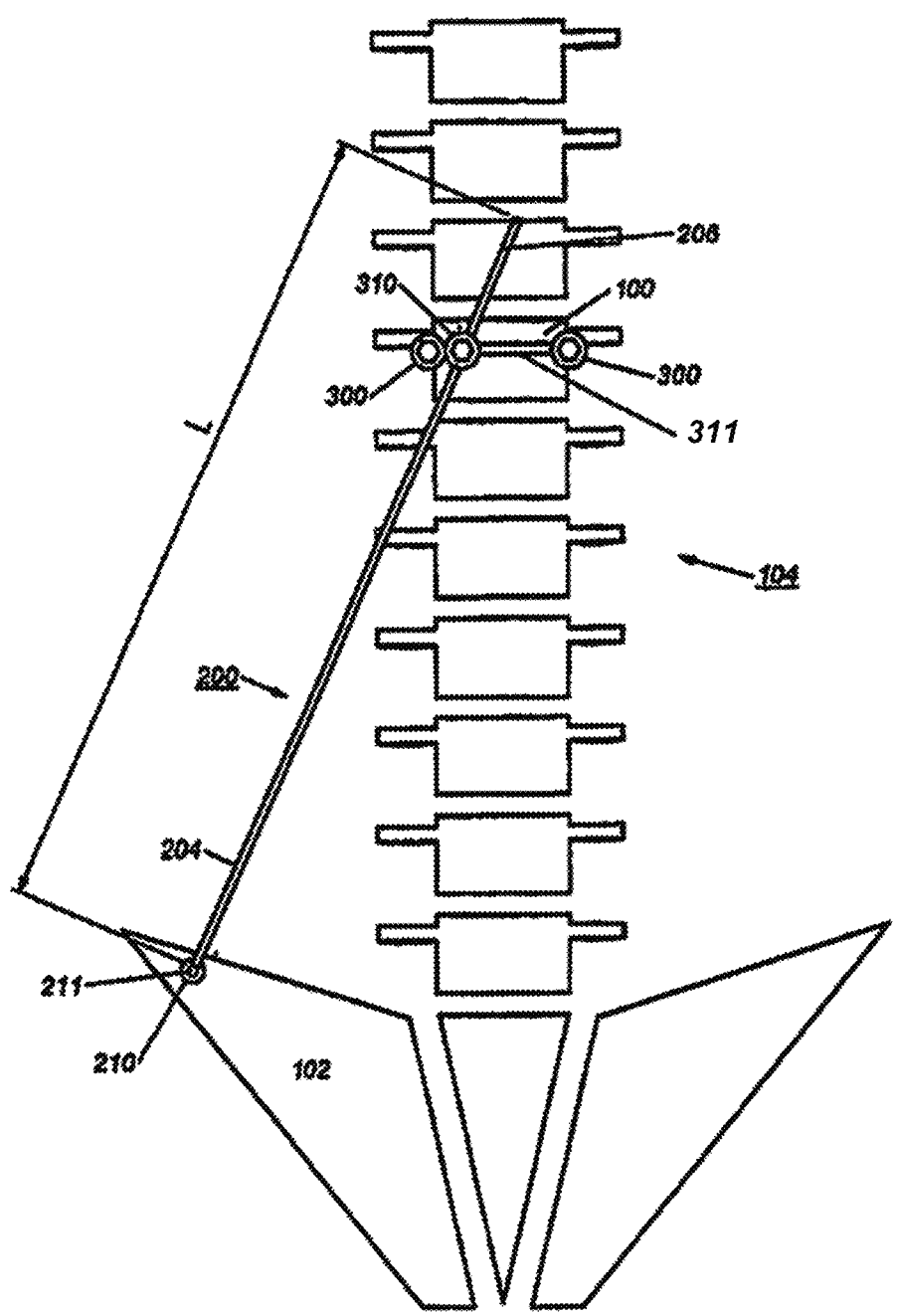
FIG. 2 is an illustration of a posterior view of a corrected human spine with the implanted device shown in FIG. 1.

FIG. 2 illustrates the correction of the spine of FIG. 1 using device 200. As illustrated in FIG. 2, the free end 206 of tether 204 is pulled and the spine is manually manipulated during the surgery to achieve a correction of the deformity. When a satisfactory curve magnitude is achieved, tether 204 is tightened within the tether clamp, effectively locking the distance between vertebra 100 and the ilium 102.

It should be noted that various levels of manipulation of the vertebral column can be coordinated using the device. For instance, different curvatures of the spine can be achieved by changing the position of the anchor and the clamp on the tether with respect to the vertebral column and the ilium. The locations along the tether where the clamp and anchor are attached determine an effective length of the tether, which in turn maximizes the distance that the attached vertebra may move relative to the position where the tether is attached at in the ilium. The scoliotic curve is corrected (or maintained) by adjusting the clamping and anchoring locations along the tether.

Figure 3:
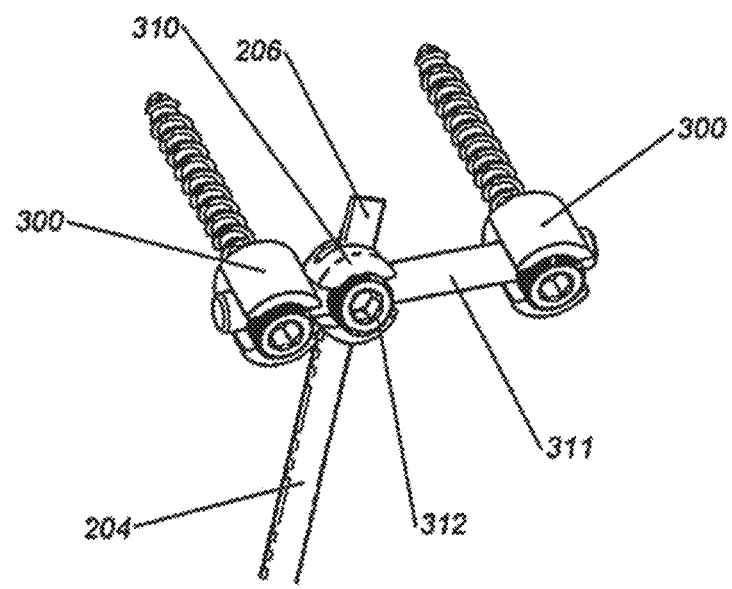
FIG. 3 shows a spinal anchoring means in the form of two pedicle screws and a rod onto which is secure an attachment mechanism and the tether.

FIG. 3 shows a detailed view of pedicle screws 300, transverse rod 311, tether clamp 310 and tether 204. In a preferred embodiment tether clamp 310 includes locking screw 312 which clamps tether clamp 310 onto rod 311 as well as locking the tether 204 within the clamp 310.

Figure 4:
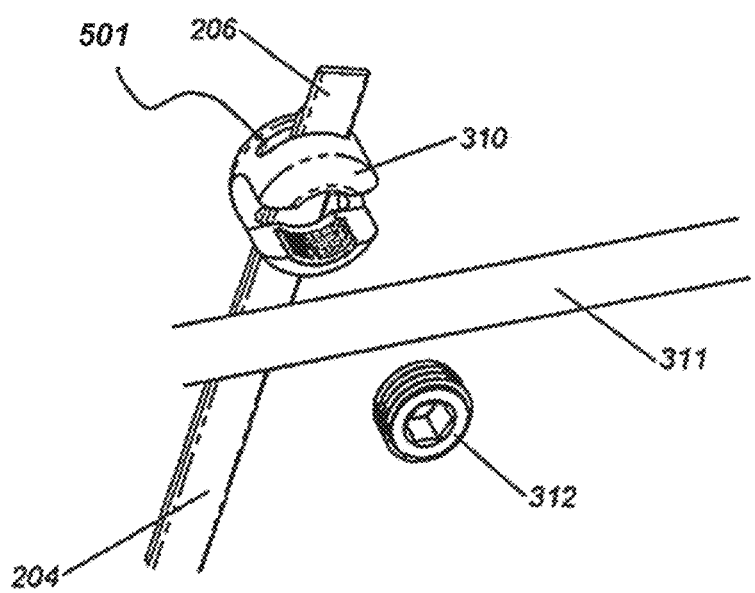
FIG. 4 illustrates an attachment mechanism and the method of attaching it to the spinal anchoring mechanism.

FIG. 4 shows a detailed view of the tether clamp 310 coupled to the transverse rod. The tether clamp 310 is configured with a slot 501 which is provided through the tether clamp 310 and tether 204 is passed through slot 501. It should be noted that the tether may be passed through the slot multiple times, if necessary. Locking screw 312 is used to secure the transverse rod 311 onto the tether clamp 310 and applies a compressive force upon the rod 311 onto the tether 204, thereby clamping the tether 204 securely in place. It should be noted that although a threaded set screw is utilized in the present embodiment, any type of locking element know in the art for securing the tether within tether clamp may be used.

Figure 5:
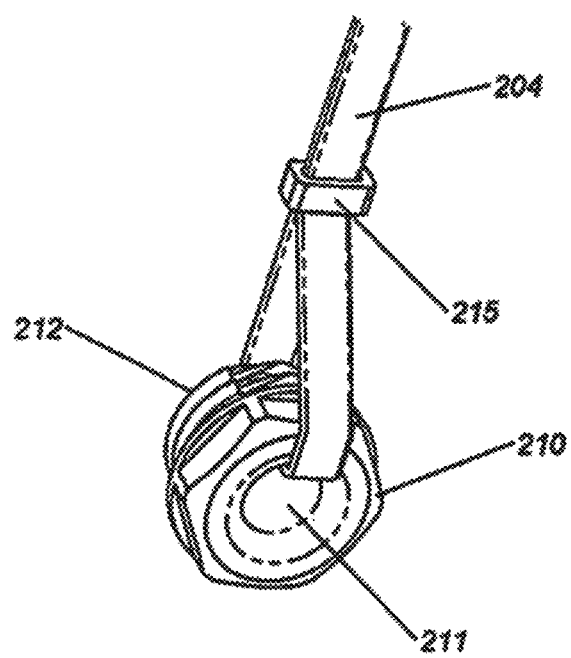
FIG. 5 shows the anchoring mechanism of the ilium (not shown) and the method of attaching the tether to it.

FIG. 5 shows a detailed view of an ilium anchor 210. Ilium anchor 210 includes threads 212 for engagement with ilium 102 (not shown). Tether 204 is passed through bore 211 and then passed back to the vertebral column. A collar 215 is shown which keeps tether 204 adjacent to itself.

Figure 6:
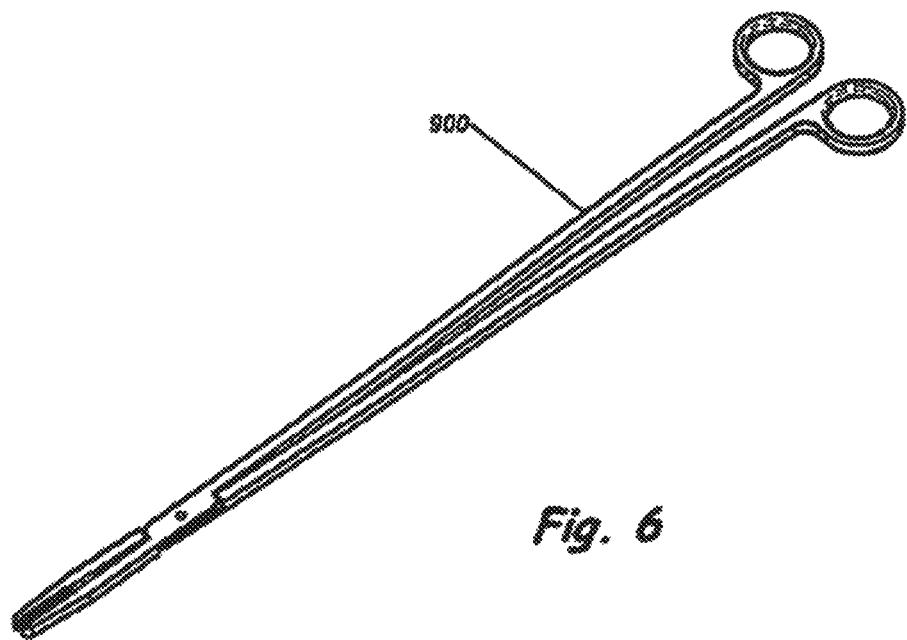
FIG. 6 shows a long pair of forceps to be used for passing the tether beneath the skin.
Figure 7:
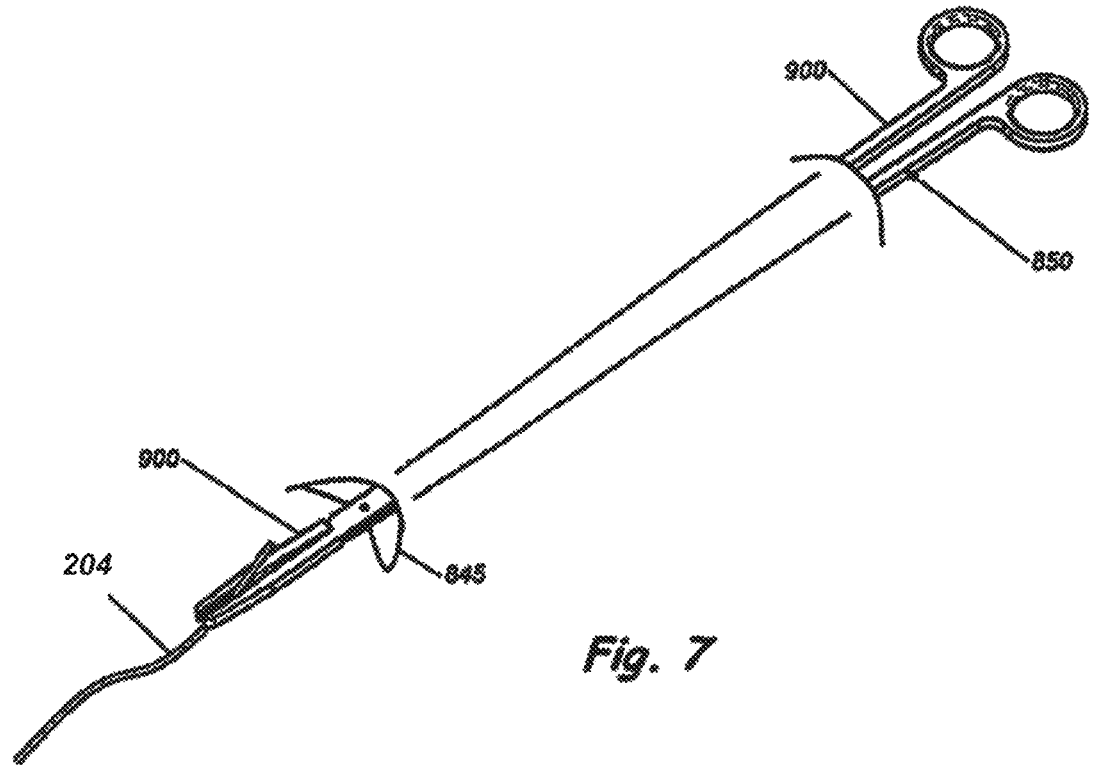
FIG. 7 illustrates the use of the forceps of FIG. 6 in passing the tether beneath the skin.

FIG. 6 shows an extra-long pair of forceps 900. FIG. 7 shows the preferred method of passing the tether through an incision 845 and underneath skin and other soft tissues. The forceps 900 are used to pass the tether though the openings in the tether clamp and used to tension the tether to correct the deformity of the curvature in the spine.

Figure 8:
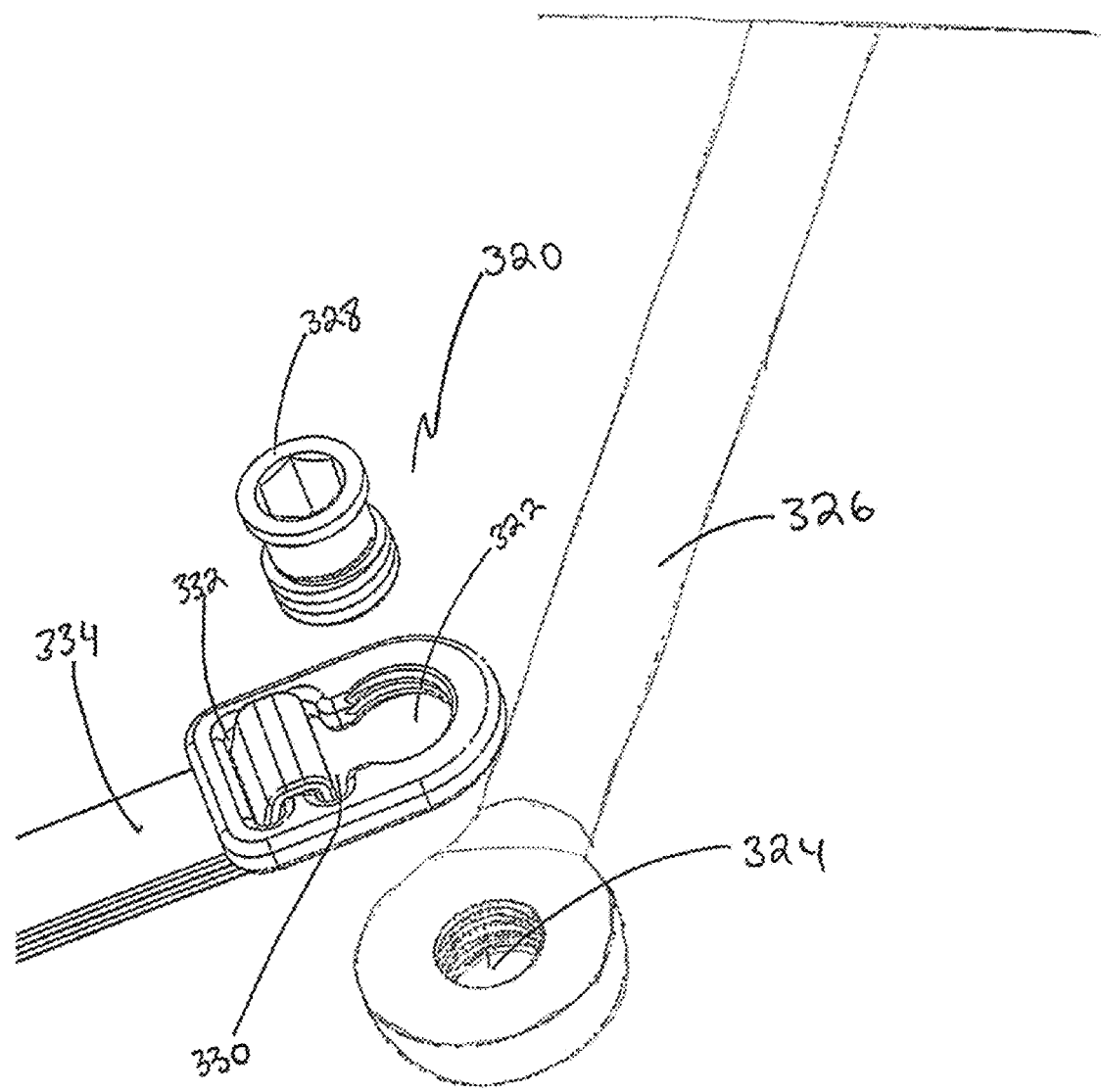
FIG. 8 illustrates an alternative embodiment of the tether clamp and elongate rod according to the present invention.

FIG. 8 illustrates another embodiment of a tether clamp 320 according to the present invention. In this embodiment, the tether clamp 320 is configured with a through hole 322 that is configured to correspond to a through hole 324 in an elongate rod 326 that is fixated to a portion of the spinal column. A fastening element 328 such as a set screw is provided to couple the tether clamp 320 and the elongate rod 326 together. The tether clamp 320 also includes openings 330, 332 which are dimensioned to receive and securely couple a tether 334 to the clamp 320. The tether 334 is pulled through each of the openings 330, 332 to securely attach the tether 334 to the clamp 320 and the elongate rod 326.

Figure 9:
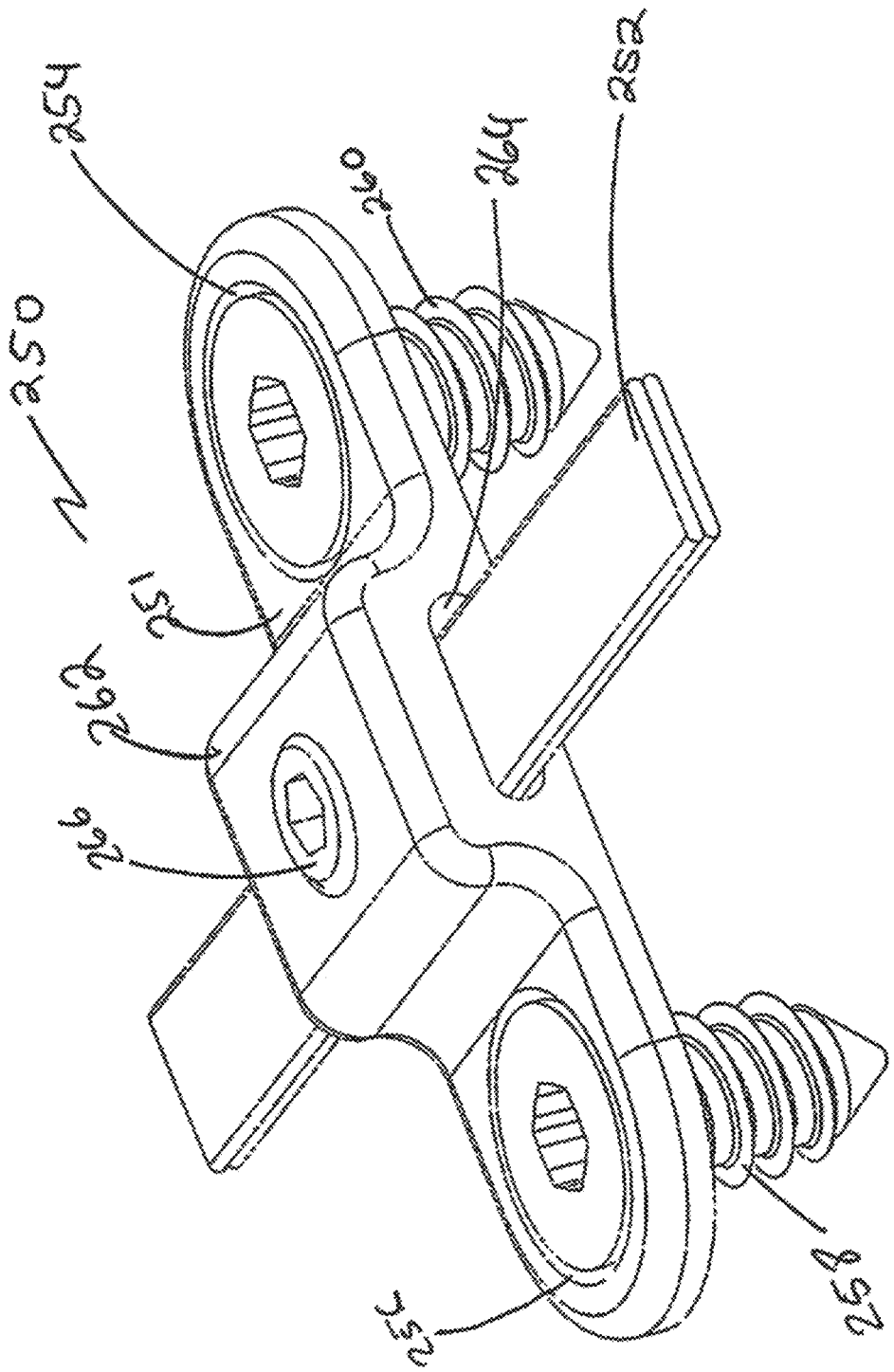
FIG. 9 illustrates another embodiment of a clamp or anchor according to the present invention.
Figure 10:
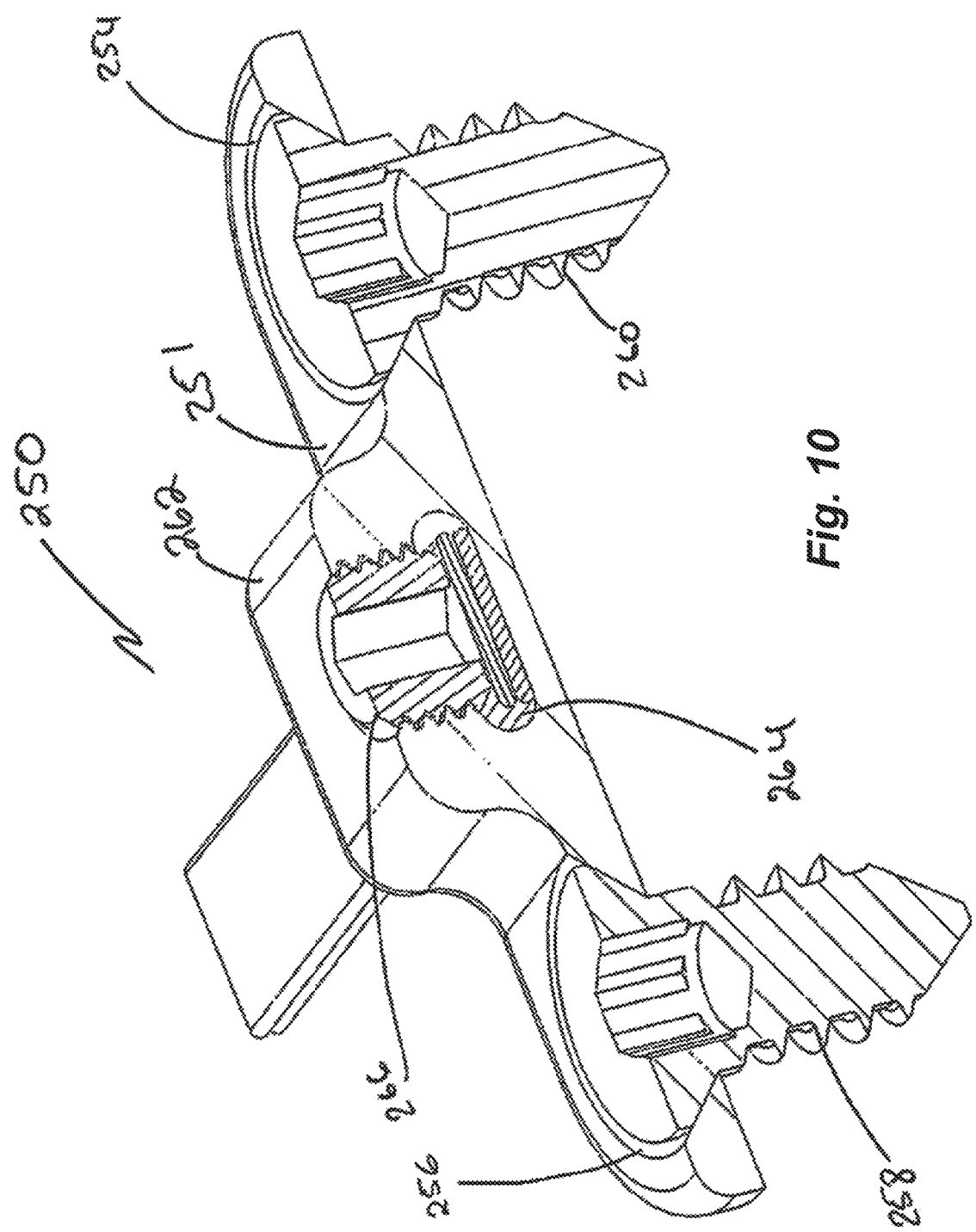
FIG. 10 shows a cross-sectional view of the device shown in FIG. 9.

FIGS. 9 and 10 illustrate an alternative embodiment of a clamp and/or anchor 250 that can be used to secure a tether 252 to either the vertebral column or a portion of the ilium. More specifically, the anchor 250 of FIGS. 9 and 10 may be configured and dimensioned to be attached to a portion of the vertebral column or may be configured be secure the tether to the ilium. The anchor 250 is configured as a plate 251 having at least two openings 254, 256 to receive fasteners 258, 260 capable of fixating the plate to bone. The plate 251 includes a middle portion 262 having an opening 264 that is capable of receiving the tether 252. The middle portion 262 of the plate 251 is further provided with a fastening element 266 to secure the tether 252 to the plate 251. As more clearly illustrated in FIG. 10, the fastening element 266 may be a set screw which directly contacts the tether 252 when tightened to secure the tether 252 to the plate 251. It should be noted that any other type of fastening element which is capable of securing the tether to the anchor may be used, such as a pin.

Figure 11:
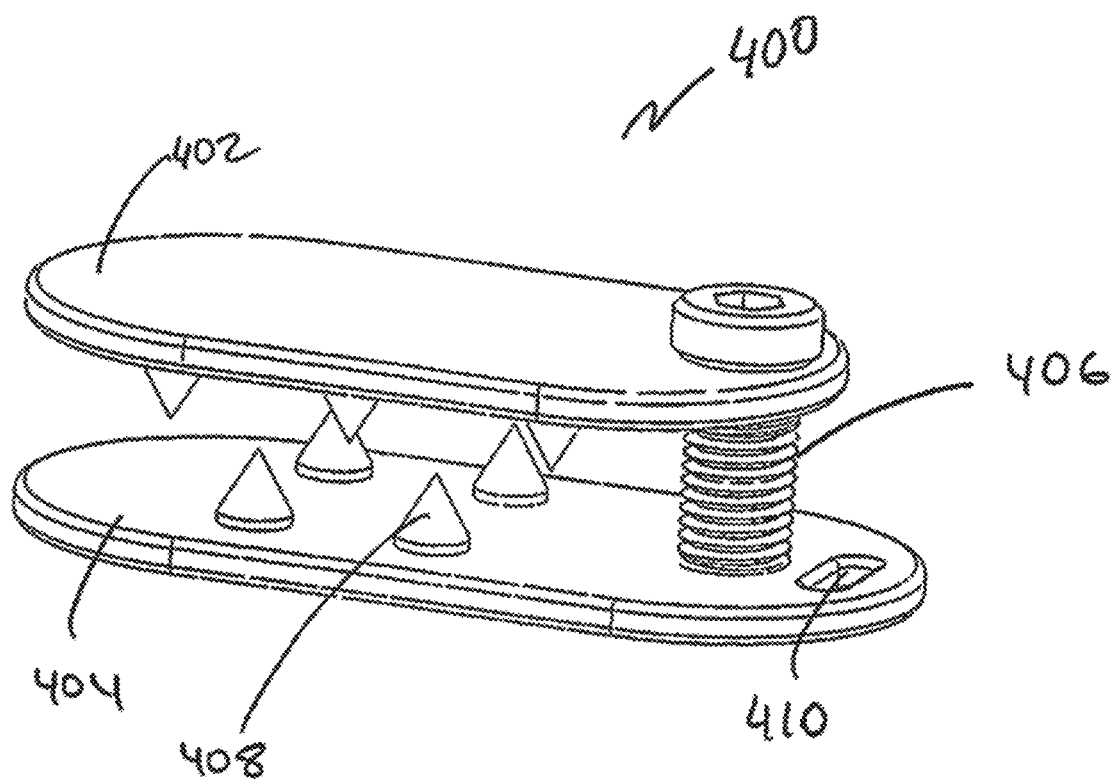
FIG. 11 shows another embodiment of a clamp or anchor according to the present invention.

FIG. 11 illustrates yet another embodiment of a clamp or anchor 400 according the present invention. In this embodiment, the clamp and/or anchor 400 includes a first plate 402 and second plate 404 that are secured to one another via a fastening element 406. The first and second plates 402, 404 are may also include spikes 408 or similar type of features that bite into bone. Either the first or second plate 402, 404 or both also includes an opening 410 for receiving a tether. The first and second plates 402, 404 are positioned so that bone is in between, such as the ilium or a portion of the vertebral column. As the first and second plates 402, 404 are compressed into bone, the tether which is positioned through the opening 410 and in between the first and second plates 402, 404, is also securely locked between the plates and the bone thereby securing the tether to the plates 402, 404. In an alternative embodiment, the tether is passed through the opening and secured to the anchor 400 by a clamp device such a belt clamp or secured by knotting the tether around the edge of the anchor 400. It should be noted that any type of mechanical mechanism to attach the tether to the anchor may be used.

Figure 12:
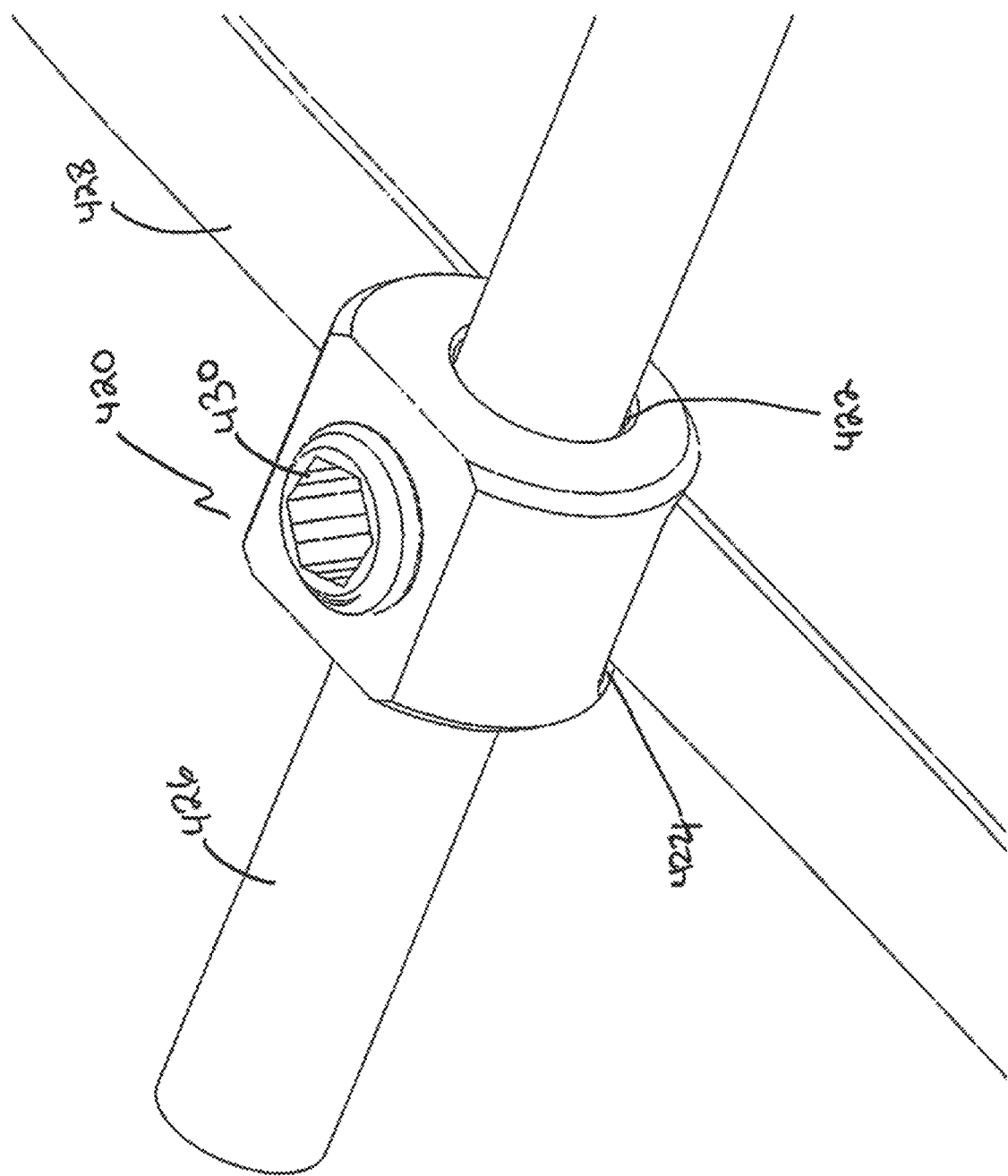
FIGS. 12 and 13 shows a closed head clamp according to the present invention.
Figure 13:
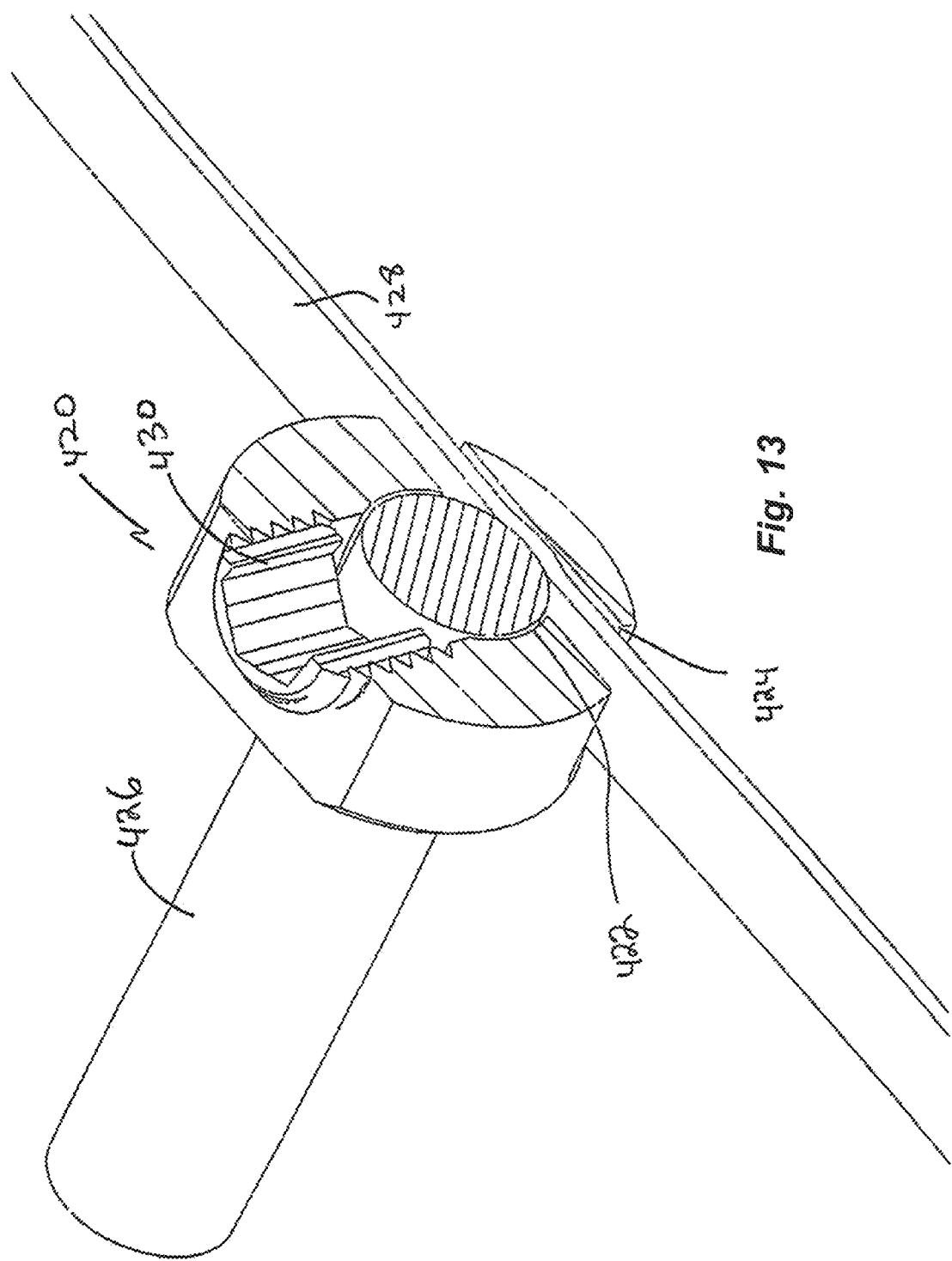

FIGS. 12-15 illustrate yet another embodiment of a clamp according to the present invention. The closed head clamp 420, as illustrated in FIGS. 12 and 13, includes a first opening 422 extending through the clamp 420 in a first direction and a second opening 424 extending in a second direction. The first and second directions are generally perpendicular to one another. The first opening 422 is configured to receive an elongate rod 426 and the second opening 424 is configured to receive a tether 428. The clamp 420 is further provided with a fastening element 430 that is used to secure both the rod 426 and the tether 428. In this embodiment, FIGS. 12 and 13 also illustrates that the second opening 424 is positioned at a bottom portion of the clamp 420, thus, as the fastening element 430 is tightened, the fastening element 430 contacts the rod 426 which is pushed against the tether 428 thereby securing the tether 428 and rod 426 within the clamp.

Figure 14:
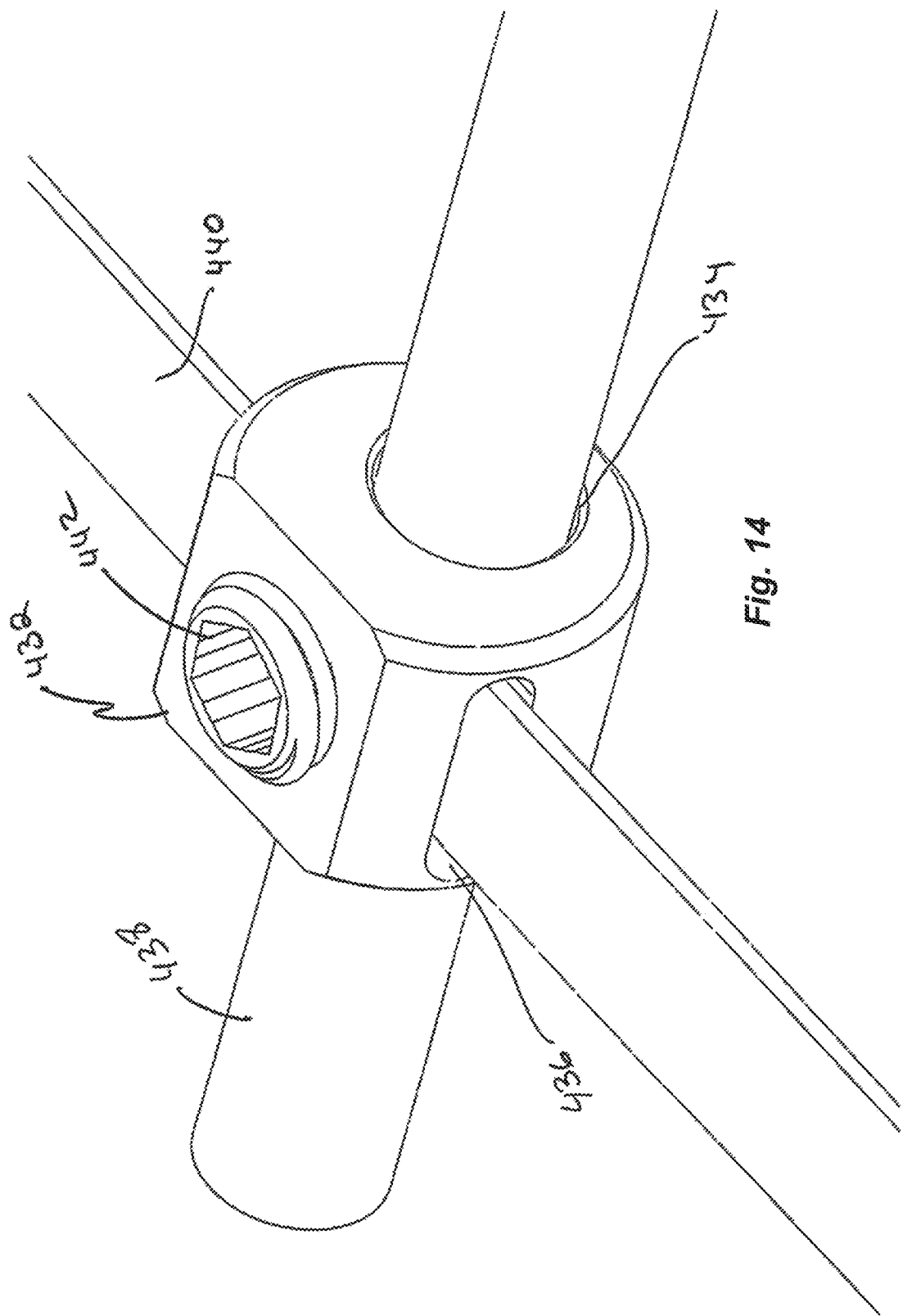
FIGS. 14 and 15 shows yet another embodiment of a closed head clamp according to the present invention.
Figure 15:
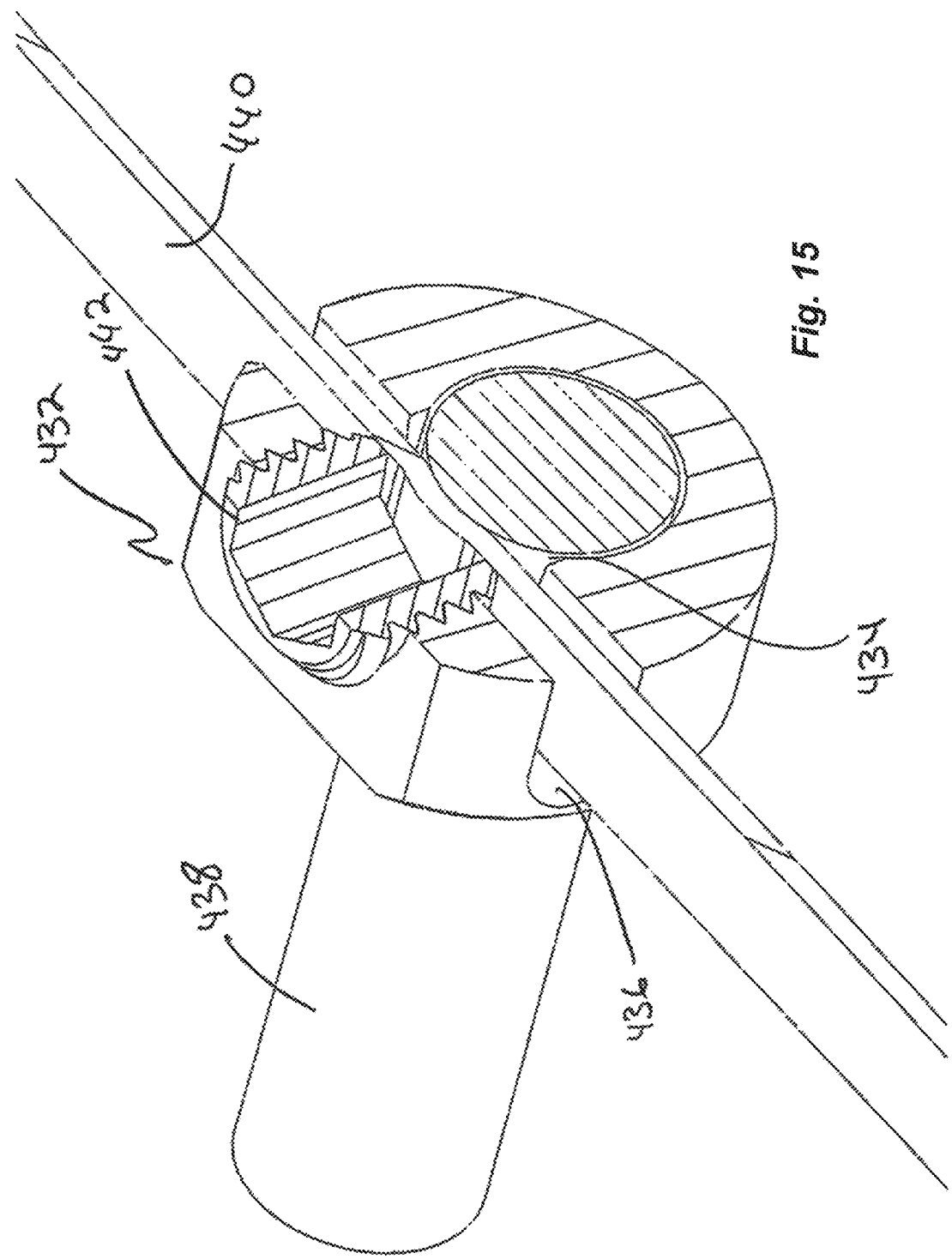

In an alternative embodiment of the closed head clamp as illustrated in FIGS. 14 and 15, the closed head clamp 432 includes a first opening 434 and a second opening 436. The first opening 434 and the second opening 436 are configured to be generally transverse to one another. The first opening 434 is dimensioned to receive an elongate rod 438 and the second opening 436 is dimensioned to receive a tether 440. The clamp 432 also includes a fastening element 442, such as a set screw, which when tightened secures and locks the tether 440 and the elongate rod 438 within the clamp 432. In this particular embodiment, the second opening 436 is positioned between the fastening element 442 and the elongate rod 438. When the fastening element 442 is tightened, the fastening element 442 directly contacts the tether 440 which contacts the elongate rod 438 thereby securely locking the tether 440 and the elongate rod 438 within the closed head clamp 432.

Figure 16:
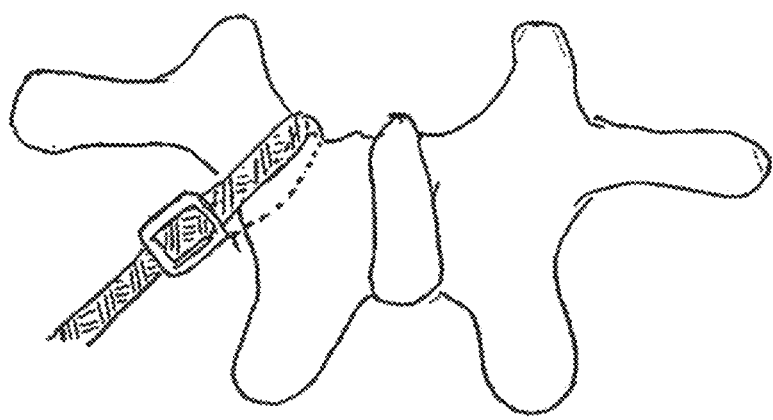
FIGS. 16-18 illustrate various methods of coupling the tether to portions of the spine and/or ilium.
Figure 17:
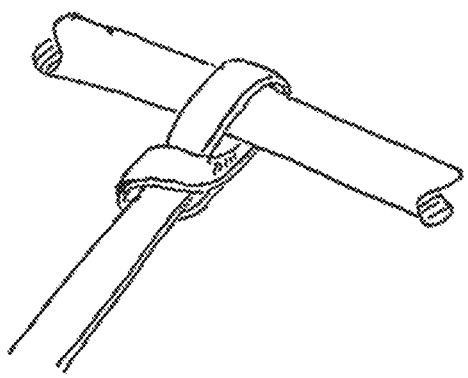
Figure 18:
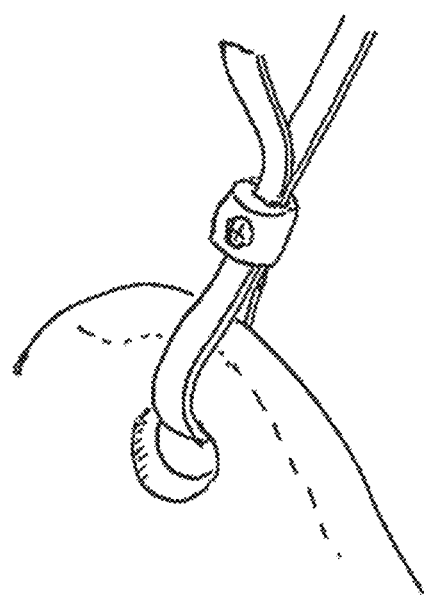

FIGS. 16-18 illustrate alternative embodiments of the inventive device. Specifically, FIG. 16 illustrates the use of clamp to attach the tether to the lamina of a vertebra. As illustrated, the tether may encircle the lamina and may be tightened using a belt clamp. In an alternative version shown in FIG. 28, the tether 204 may be looped around the lamina 106 and a force F applied to the tether 204. The other end of the tether is as shown in the earlier embodiments coupled to a portion of the ilium. Using this mechanism, the deformity of the spine may be corrected by manipulating the tether as well as the positioning of the clamp, as needed.

FIG. 17 shows a tether that includes a loop which is used to for coupling the tether to the transverse rod to fixate the tether to the transverse rod. FIG. 18 illustrates the coupling of the tether directly to the ilium using another type of tether clamp. It should be noted that in the examples provided of both anchor and clamps, these mechanical devices may be interchangeable.

It should also be noted that the tether of the present invention may be composed of fabric, polymer, such as PET, or any other biocompatible materials. The tether can be a cable and can be dimensioned to be a wide elastic band which advantageously reduce the risk of damage to tissue lacerations or injury. In some embodiments, the tether can be is between 2 and 900 mm. Also, to ensure that proper correction of deformities, a tensioner can be included as part of the system to make sure that the tether is in proper tension and tightness.

FIGS. 19-21 show an alternative version of a tether clamp 520. Similar to tether clamp 320, tether clamp 520 is configured to couple a tether 204 to an elongate rod 326. FIG. 19 shows the clamp 520 in an open configuration. FIG. 20 shows the clamp 520 in a closed configuration with a fastener 528. FIG. 21 depicts the clamp 520 attached to an elongate rod 326 with fastener 528. The tether clamp 520 is in the form of a hinged clamp configured to clamp the tether 204 and connect the tether 204 to the rod 326. The hinged tether clamp 520 includes a main clamp body 524, a hasp body 526 hingedly connected to the clamp body 524, and a fastener 528 (such as a screw) configured to secure the hasp body 526 to the clamp body 524 and the clamp 520 to the elongate rod 326. The hasp body 526 is able to pivotally move with respect to the clamp body 524 to allow for the open and closed configurations.

The clamp body 524 may extend from a distal end to a proximal end. The clamp body 524 may include a through hole 522 extending through the clamp body 524. The through hole 522 may be positioned closer to the distal end of the clamp body 524. The through hole 522 may by generally spherical in cross-section and sized and dimensioned to receive at least a portion of the fastener 528. The inner surface of the through hole 522 may be non-threaded or threaded. Preferably, the inner surface of the through hole 522 is threaded to mate with corresponding threads on the fastener 528.

The clamp body 524 further includes a first elongate opening 530 extending through the clamp body 524 and a second elongate opening 532 extending through the clamp body 524. The second elongate opening 532 may be positioned closer to the proximal end of the clamp body 524, and the first elongate opening 530 may be positioned between the through hole 522 and the second elongate opening 532. The first elongate opening 530 may be separate and distinct from the through hole 522, as shown in the embodiment FIG. 19, or may join to form a single irregular opening, as shown in the embodiment in FIG. 22. The second elongate opening 532 may be defined by the clamp body 524 or the second elongate opening 532 may be created by the hinge of the clamp 520. The first and second elongate openings 530, 532 may be substantially parallel to one another. The first and second elongate openings 530, 532 are preferably sized and dimensioned to receive the corresponding width and thickness of the tether 204. Thus, the tether 204 is configured to be received by and through the first and second elongate openings 530, 532 in any suitable configuration to at least temporarily hold the tether 204 in the clamp body 524.

A preferred way of threading the tether 204 to the clamp body 524 is shown in FIG. 19 by arrow A. As shown by arrow A, a free end 206 of the tether 204 is passed through the first elongate opening 530 in the clamp body 524 and back through the second elongate 532 such that the tether 204 substantially folds back onto itself. When the tether 204 is passed through the clamp body 524 (as shown by arrow A), the clamp 520 will temporarily hold the position of the tether 204 when the tether 204 is tensioned. Thus, the tether 204 may be appropriately tensioned by pulling on the free end 204 of the tether 204 and advancing the tether 204 through the first and second elongate openings 530, 532. Similarly, the tension may be reduced by allowing the tether 204 to retract back through the first and second elongate openings 530, 532.

Once the tether 204 is appropriately tensioned, the hasp body 526 may be closed into contact with or close into contact with the clamp body 524. The hasp body 526 also extends from a distal end to a proximal end. The distal end of the hasp body 526 forms a hinge sleeve portion 534. The hinge sleeve portion 534 may have an opening extending longitudinally therethrough sized and configured to receive a pivot pin 536. The opposing ends of the pivot pin 536 are each configured to be received in and engage one or more openings extending through the clamp body 524. Thus, the pivot pin 536 enables the hasp body 526 to pivot or angulate with respect to the clamp body 524. For example, the hasp body 526 may be positioned at an angle ranging from about 45-180°, about 50-120°, about 60-110°, about 70-100°, or about 90° relative to the clamp body 524, when in an opened position.

The hasp body 526 includes a through hole 538 extending through the hasp body 526. The through hole 538 may be positioned closer to the distal end of the hasp body 526. The through hole 538 may by generally spherical in cross-section and sized and dimensioned to receive at least a portion of the fastener 528. The inner surface of the through hole 538 may be non-threaded or threaded. When the hasp body 526 is aligned with the clamp body 524, the through hole 538 of the hasp body 526 aligns with the through hole 522 of clamp body 524. As shown in FIG. 20, when the through holes 522, 538 are aligned, fastener 528 may be inserted therethrough to lock the tether 204 to the clamp 520. The through hole 538 of the hasp body 526 may be substantially the same size or larger than the through hole 522 of clamp body 524. The through hole 538 is preferably sized larger to receive a head portion 540 of the fastener 528 when recessed into the hasp body 526.

Referring to FIG. 21, the fastener 528 is attachable to the clamp 520 and the rod 326 in order to compress the tether 204 between the hasp body 526 and the clamp body 524, thereby providing a more substantial, permanent hold. The fastener 528 may include a head portion 540 and a shaft portion extending therefrom. The head portion 540 may include a recess sized and configured to receive a driving instrument, such as a hex driver, in order to rotate and insert the fastener 528 through the through holes 538, 522 and into an opening 324 in the elongate rod 326. Thus, the fastener 528, when tightened, causes the hasp body 526 including the hinge sleeve portion 534, which may be enlarged relative to the rest of the hasp body 526, to squeeze the tether 204 between the clamp body 524 and the hasp body 526 and/or hinge sleeve portion 534 to permanently secure the tether 204 in position. The hinge sleeve portion 534 is preferably sized and dimensioned to apply an appropriate force to the tether 204 to secure the tether to the clamp 520. As shown, the hinge sleeve portion 534 may have a generally cylindrical or partially spherical shape, which is enlarged relative to the rest of the hasp body 526, to further tighten the tether 204 when the hasp body 526 is rotated to the closed position.

Figure 22:
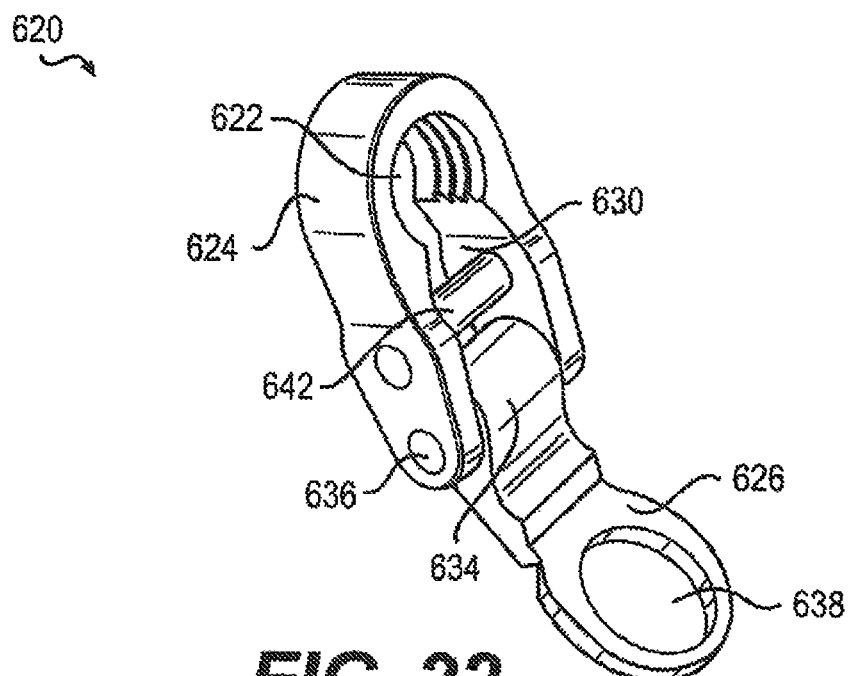
FIGS. 22 and 23 provide yet another alternative for a tether clamp.
Figure 23:
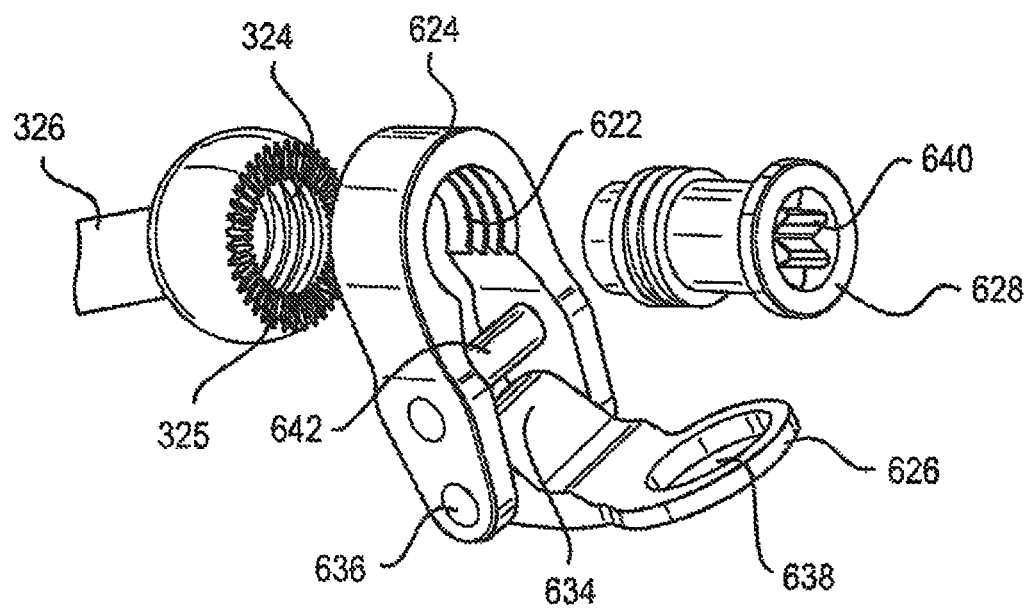

Referring now to FIGS. 22 and 23, another version of a tether clamp 620, in the form of a hinged clamp, configured to clamp the tether 204 with the clamp 620 is shown. Similar to tether clamp 520, the hinged tether clamp 620 includes a main clamp body 624, a hasp body 526 hingedly connected to the clamp body 624, and a fastener 628 configured to secure the hasp body 626 to the clamp body 624 and the clamp 620 to the elongate rod 326. FIG. 22 shows the clamp 620 in an open configuration, and FIG. 23 shows an exploded view of the clamp 620, elongate rod 326, and fastener 628.

As shown in FIG. 22, the clamp body 624 may have a generally U-shaped body. The clamp body 524 may include a through hole 622 extending through the clamp body 624. The through hole 622 may have a partial-spherical cross-section and sized and dimensioned to receive at least a portion of the fastener 528. The inner surface of the through hole 622 may be threaded to mate with corresponding threads on the fastener 628. The clamp body 624 further includes an enlarged opening 630 extending through the clamp body 624. The enlarged opening 630 and through hole 622 may join to form a single irregular opening (e.g., a key-shaped opening defined by the outer U-shaped clamp body 624). An elongate pin member 642 may connect a first side to a second side of the U-shaped clamp body portion 624. In particular, opposing ends of the pin member 642 are each configured to be received in and engage one or more openings extending through the clamp body 624. The tether 204 is configured to be received around the elongate pin member 642 in any suitable configuration to at least temporarily hold the tether 204 in the clamp body 624. The tether 204 may be looped around the pin member 642 and in direct contact with the pin member 642 for temporary attachment.

Similar to the threading of the tether 204 shown in FIG. 19, a free end 206 of the tether 204 may be passed through the space between the through hole 622 and the pin member 642 in the clamp body 624 and back through the space between the pin member 642 and the hinge sleeve portion 634 such that the tether 204 substantially folds back onto itself. The clamp 620 will temporarily hold the position of the tether 204 as the tether 204 is appropriately tensioned to correct the spinal deformity.

The hasp body 626 includes a through hole 638 extending through the hasp body 626. When the hasp body 626 is aligned with the clamp body 624, the through hole 638 of the hasp body 626 aligns with the through hole 622 of clamp body 624 and fastener 628 may be inserted therethrough to lock the tether 204 to the clamp 620. Once the tether 204 is appropriately tensioned, the hasp body 626 may be closed into contact with or close into contact with the clamp body 624. The distal end of the hasp body 626 forms an enlarged hinge sleeve portion 634 including an opening extending longitudinally therethrough sized and configured to receive a pivot pin 636. The opposing ends of the pivot pin 636 are each configured to be received in and engage one or more openings extending through the clamp body 624. Thus, the pivot pin 636 enables the hasp body 626 to pivot or angulate relative to the clamp body 624 and allows for open and closed configurations of the clamp 620.

The fastener 628 may include a head portion 640 and a shaft portion extending therefrom. A portion of the shaft portion may be threaded, as shown in FIG. 23. The shaft portion may be threaded along the entire length or any suitable portion thereof. Preferably, at least the portion of the shaft in contact with the through hole 622 in the clamp body 624 and the opening 324 in the elongate rod 326 is threaded. The head portion 540 may include a recess sized and configured to receive a driving instrument, such as a hex driver, in order to rotate and insert the fastener 628 through the through holes 638, 622 and into an opening 624 in the elongate rod 626.

As best seen in FIG. 23, the elongate rod 626 and clamp 620 may further include a clutch feature in the form of radial grooves 325 and corresponding radial grooves (not visible) on the back of the clamp 620 so that no counter-torque instrument is needed to prevent rotation of the clamp 620 during tightening of the fastener 628. The radial grooves 325 may be in the form of radial slots, protrusions, or the like extending around the opening 324 in the elongate rod 326. The corresponding radial grooves include mating radial slots, protrusions, or the like extending around the opening 622 in the clamp body 624. The fastener 628 is attachable to the clamp 620 and the rod 626 in order to compress the tether 604 between the hasp body 626 and the clamp body 624, thereby providing a more substantial, permanent hold. Thus, the fastener 628, when tightened, squeezes the tether 204 between the clamp body 624 and the hasp body 626 to permanently secure the tether 604 in position.

Figure 24:
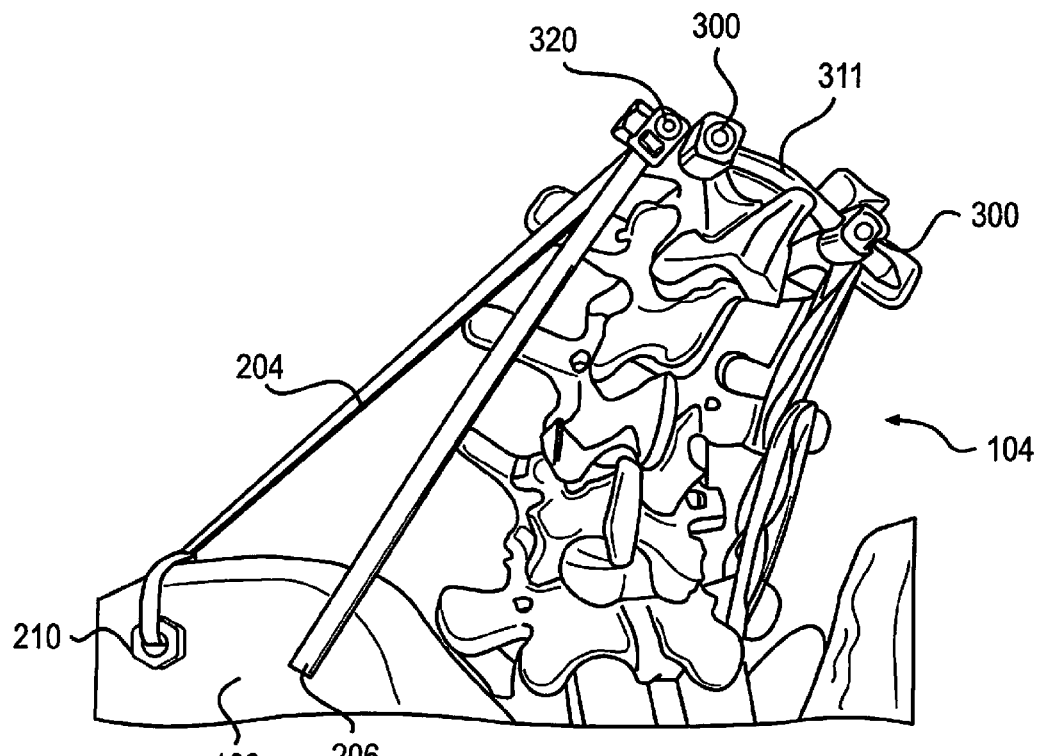
FIGS. 24 and 25 depict a posterior view of a deformed human spine and a corrected human spine, respectively, with an implanted device according to one embodiment.
Figure 25:
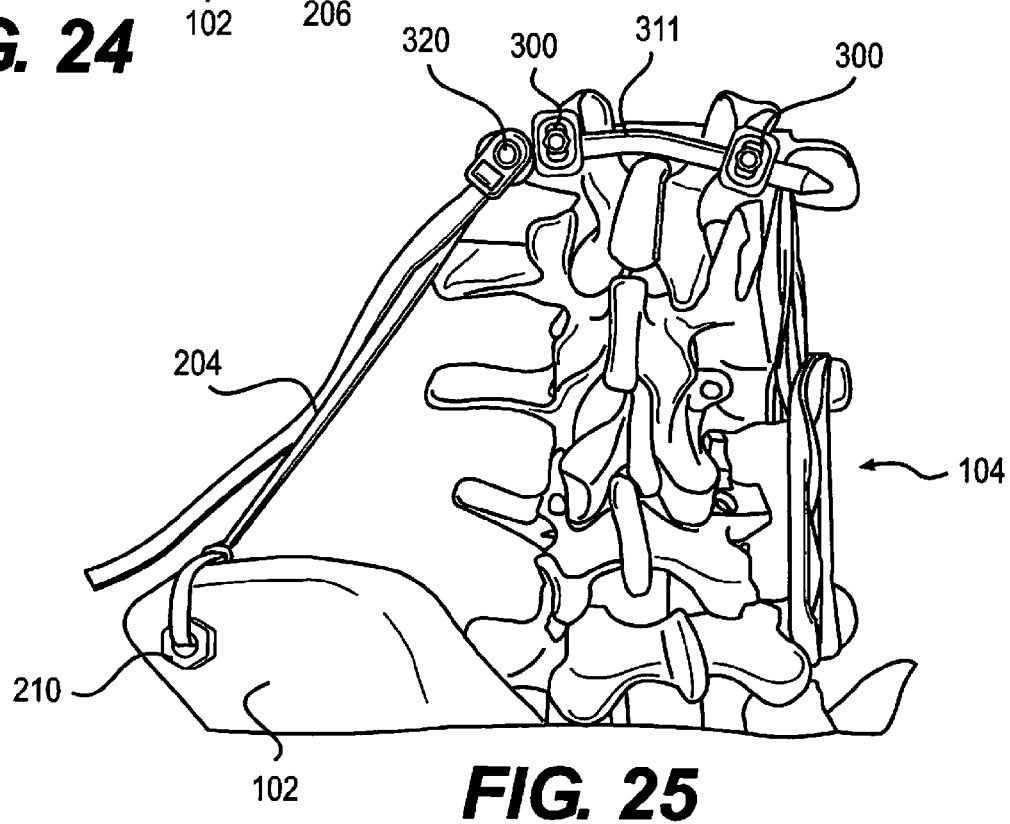

Referring now to FIGS. 24 and 25, correcting a spinal deformity, such as scoliosis, is described further. FIG. 24 depicts a posterior view of a deformed human spine 104 with an implanted device, and FIG. 25 depicts a posterior view of a corrected human spine 104 after the tether 204 has been tensioned. As described elsewhere in this document, the implanted device may include two attachment mechanisms, such as pedicle screws 300, which are anchored to the vertebra of the spine by insertion into opposing pedicles, and a transverse rod 311 connected between the pedicle screws 300.

An ilium anchor 210 is attached to the ilium 102 to secure one end of the tether 204. The ilium anchor 210 may be in the form of a bushing inserted through a hole drilled in the ilium 102. The anchor 210 may have threads on its exterior surface to bite into the bone. The exterior surface may also include a coating of porous material, hydroxyapatite, bioconductive material, and/or bioinductive material. The tether 204 may be passed through the anchor 210 and secured, for example, with a buckle, a loop, or other connection mechanism. The free end 206 of the tether 204 is passed through a tether clamp, for example, tether clamp 320 described elsewhere herein or any other suitable tether clamp. The tether clamp 320 may be attached to the transverse rod 311 at any suitable location along its length. For example, the tether clamp 320 may be connected to the transverse rod 311 at one end of the transverse rod 311. The tether 204 may be tensioned until the deformity is corrected as shown in FIG. 25.

The tether system may have a number of advantages. Because the tether 204 connects the spine 104 to the ilium 102, the tether 204 uses the pelvis as a foundation from which to exert corrective forces onto a scoliotic spine. The tether system is not in the axial load path of the spine so forces typically borne by the spine continue to be borne by the spine. There may be no need for fusion during the life of the implant, but the system may be used prior to fusion if desired (e.g., a surgeon may use the tether system to prevent curve progression or correct a curve and then later fuse the spine with a subsequent surgery). The procedure is minimally invasive and may reduce operating room time and/or recovery time. The tether 204 is adjustable with a small incision to accommodate progressive correction and to prevent overcorrection during growth modulation procedures.

Referring now to FIGS. 26 and 27, a method and device for scoliosis correction are shown. In particular, the device and method may include de-rotating the vertebra in the axial plane. While traditional scoliosis correction attempts to laterally shift the spine, this method de-rotates the spine because axial rotation and lateral shift are mechanically coupled in the thoracic spine by the ribcage. In other words, axial rotation of one or more vertebra correlates to a lateral shift in the spine and correction of the scoliotic spine. This method does not need to involve fusion to correct the spinal deformity.

As shown in FIG. 26, a non-fusion implant 700 may be used to impose a de-rotating tension on a pedicle screw 702 by using the posterior-most aspect of the ribs 110 as an anchor point. The implantation may be a minimally invasive surgical procedure, for example, through a small midline incision. The implant 700 may include one or more plates 704 configured to contact the ribs 110 and a pedicle screw 702 extending through the plate 704. The plate 704 may be substantially straight, curved, or contoured as necessary to extend to the posterior-most aspect of the ribs 110 on either side of the vertebra 108.

The plate 704 may be implanted to abut the posterior aspect of the ribs 110 on both sides of the patient. The plate 704 may be coupled to the ribs 110 or may merely contact the ribs 110 without coupling thereto. The pedicle screw 702 with a threaded shank 706 may be passed through a slot 708 in the plate 704. The slot 708 may be sized to receive the shank 706 or may be elongated to allow for movement of the shank 706 along the length of the plate 704. A coupling element, such as a nut 710, may be used to secure the screw 702 to the plate 704. By rotating the nut 710 onto the threaded shank 706, the pedicle is pulled closer to the plate 704. This action causes de-rotation of the vertebra 108 and alignment of the spine. The de-rotation can be performed acutely or progressively over a period of time by re-accessing the nut 710 with a small incision and adjusting at one or more different points in time after the initial surgery.

In another embodiment, shown in FIG. 27, instead of coupling with a nut, the threaded shank 706 may be received in a coupling sleeve 712. The coupling sleeve 712 may include a threaded opening extending longitudinally therethrough sized and dimensioned to receive the threaded shank 706 of the screw 702. The coupling sleeve 712 may include an enlarged head portion configured to engage with the slot 708 in the plate 704. By rotating the coupling sleeve 712 onto the threaded shank 706, the pedicle is once again pulled closer to the plate 704 in order to de-rotate the vertebra 108 in the axial plane. Although depicted entering one pedicle of the vertebra 108, it is envisioned that the pedicle screw 702 could enter the opposite pedicle screw to apply torque to the vertebra 108 in the other direction. Alternatively, if pedicle screws cannot be used, for example, in the case of a small pediatric patient, a sublaminar band or wire can be attached to the plate 704 and tensioned as necessary to provide the desired axial movement. Regardless of the mechanism, the axial rotation of one or more vertebrae provides for a lateral shift in the spine and correction of the deformity.

It will be apparent to those skilled in the art that various modifications and variations can be made in the present invention without departing from the scope or spirit of the invention. Moreover, the improved bone screw assemblies and related methods of use need not feature all of the objects, advantages, features and aspects discussed above. Thus, for example, those skilled in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed bone screw assemblies. Thus, it is intended that the present invention cover the modifications and variations of this invention provided that they come within the scope of the appended claims or their equivalents.

What is claimed is:

1. A spinal system for correcting a deformity in the spine, the system comprising:
  a tether having a distal portion and a proximal portion;
  an anchor configured to be positioned on a portion of the ilium, the anchor receiving the proximal portion of the tether;
  an elongate rod and two bone fasteners configured to be secured to a vertebra;
  a clamp configured to be secured to the elongate rod, the clamp receiving the distal portion of the tether therein, the clamp having a clamp body and a hasp body connected to the clamp body by a first pin, the clamp body having a first opening extending through the clamp body, and the hasp body having a second opening extending through the hasp body, wherein when the clamp is closed, the first and second openings are aligned with one another;
  a second pin configured to couple a first side to a second side of the clamp,
  a fastener configured to be received through the first opening in the clamp body and the second opening in the hasp body in order to securely lock the tether within the clamp
  wherein the tether is configured to be received around the second pin temporarily.

2. The system of claim 1, wherein the clamp body includes a first elongate opening and a second elongate opening extending through the clamp body, the first and second elongate openings configured to receive the distal portion of the tether to temporarily hold the tether in the clamp.

3. The system of claim 1, wherein the clamp body includes a U-shaped clamp body portion.

4. The system of claim 1, wherein the hasp body includes a hinge sleeve portion having an opening extending therethrough, and a pivot the first pin is received in the opening and connects to the clamp body to allow for pivotal movement of the hasp body relative to the clamp body.

5. The system of claim 1, wherein the fastener couples the clamp to the elongate rod.

6. The system of claim 1, wherein the elongate rod includes radial grooves and the clamp body includes corresponding radial grooves around the first opening to improve connection between the clamp and the elongate rod when tightening the fastener.

7. The system of claim 1, wherein the first opening extending through the clamp body is threaded to mate with corresponding threads on the fastener.

8. The system of claim 1, wherein the clamp is positioned on one end of the elongate rod.

9. The system of claim 1, wherein the fastener is a set screw with an enlarged head having a shall extending therefrom and a threaded portion along the shaft.

10. The system of claim 1, wherein when the fastener is tightened, the fastener applies a force against the tether to securely lock both the tether in the clamp and the clamp to the elongate rod.

11. The system of claim 1, wherein the anchor includes threads configured for engagement to the ilium.

12. A spinal system comprising:
 a clamp for coupling to an elongate rod, the clamp having a clamp body and a hasp body connected to the clamp body by a first pin, wherein the clamp body and the hasp body each comprise an opening for receiving a fastener, and the clamp body includes tether receiving openings configured to receive and secure a first portion of a tether;
 a fastener received in the openings of the hasp body and the clamp body for securing the tether to the elongate rod;
 an anchor having a bore hole configured to be positioned on the ilium, the anchor receiving a second portion of the tether,
 a second pin configured to couple a first side to a second side of the clamp,
 wherein the tether is configured to be received around the second pin temporarily,
 wherein when the fastener is secured into the openings of the hasp body and the clamp body, the tether is secured to the elongate rod.

13. The spinal system of claim 12, wherein the tether is looped through the tether receiving openings of the clamp.

14. The spinal system of claim 12, wherein the hasp body includes a hinge sleeve portion having an opening extending therethrough, and the first pin is received in the opening and connects to the clamp body to allow for pivotal movement of the hasp body relative to the clamp body.

15. The spinal system of claim 12, wherein the elongate rod includes radial grooves and the clamp body includes corresponding radial grooves around the opening for receiving the fastener to improve connection between the clamp and the elongate rod when tightening the fastener.

* * * * *